United States Patent

Babb et al.

[11] Patent Number: 5,291,879
[45] Date of Patent: Mar. 8, 1994

[54] CARBON DIOXIDE DETECTION (II)

[76] Inventors: Albert L. Babb; Michael P. Hlastala; Gary L. Tarbox, all of c/o Meridian Medical Corporation, 4811 Forest Ave. SE., Mercer Island, Wash. 98040

[21] Appl. No.: 918,372

[22] Filed: Jul. 23, 1992

Related U.S. Application Data

[63] Continuation of Ser. No. 629,055, Dec. 14, 1990, Pat. No. 5,197,464, and a continuation of Ser. No. 464,709, Jan. 12, 1990, abandoned, which is a continuation of Ser. No. 315,730, Feb. 24, 1989, abandoned, which is a continuation-in-part of Ser. No. 160,863, Feb. 26, 1988, abandoned.

[51] Int. Cl.$^5$ ............................................ A61M 16/00
[52] U.S. Cl. .......................... 128/200.26; 128/205.23; 128/207.14
[58] Field of Search ................ 128/200.26, 205.23, 128/202.22, 207.14, 207.15

[56] References Cited

U.S. PATENT DOCUMENTS 4,790,327  12/1988  Despotis ................... 128/205.23
4,928,687  5/1990  Lampotang et al. .......... 128/205.23

Primary Examiner—Edgar S. Burr
Assistant Examiner—Aaron J. Lewis
Attorney, Agent, or Firm—Hughes & Multer

[57] ABSTRACT

Methods and apparatus for ascertaining whether there is at least a threshold concentration of carbon dioxide in gases being monitored. Reversible hydration of the carbon dioxide to generate excess hydrogen ions and trigger a color change in a pH sensitive indicator is employed in representative embodiments of the invention to provide an indication that the threshold concentration of carbon dioxide is present in the gases. The methods and apparatus may be used to distinguish between tracheal and esophageal intubation of human and other mammalian patients.

1 Claim, 3 Drawing Sheets

5,291,879

CARBON DIOXIDE DETECTION (II)

CROSS REFERENCE TO A RELATED APPLICATION

This application is a continuation of application No. 07/629,055 filed 14 Dec. 1990 now Pat. No. 5197464 issued Mar. 30, 1992 by Albert L. Babb et al. for CARBON DIOXIDE DETECTION (II). Application No. 07/629,055 is a continuation of application No. 07/464,709 filed 12 Jan. 1990 (now abandoned) which is a continuation of application No. 07/315,730 filed 24 Feb. 1989 (now abandoned); and the latter is a continuation-in-part of application No. 07/160,863 filed 26 Feb. 1988, which is also abandoned.

TECHNICAL FIELD OF THE INVENTION

In one aspect, the present invention relates to novel, improved methods and apparatus for providing an indication if at least a threshold level of carbon dioxide is present or reached in a gas stream or sample of interest.

In another, and equally important, aspect, the present invention relates to novel, improved methods and apparatus for ensuring that an airway (or endotracheal) tube is properly placed in the trachea of a patient and not in the patient's esophagus.

And, in a third and also equally important aspect, the present invention relates to novel, improved methods for increasing the shelf life of detectors used for the purposes identified in the two preceding paragraphs and to the resulting detectors.

Medical applications of the invention area of particular importance at the present time, and the principles of the present invention will accordingly be developed primarily with reference to such applications. It is to be understood, however, that this is being done for the sake of convenience and clarity and is not intended to limit the scope of protection sought herein.

BACKGROUND OF THE INVENTION

Just a few decades ago, an unexpected death or serious mishap during surgery was viewed as a tragic but unavoidable event by patients and their families, and by the public at large. Lawsuits were rare, and settlements were modest.

Today, the average patient in reasonable health who enters a hospital fully expects clinicians to provide care with a near-zero risk of complication or death. If a procedure leads to loss of life or major impairment, the damage is no longer regarded as acceptable, especially when it is thought to be the result of avoidable technical or human failure. These incidents now lead to major malpractice suits against hospitals and physicians.

One of the most important aspects of critical care is the clinician's management of the patient's airway. Typically, this involves placement of an endotracheal (or airway) tube in the trachea of the patient. Oral intubation of the human trachea has become a routine procedure used to maintain a clear airway in most surgical, emergency, and intensive care situations. Intubations are performed in the hospital and in the field by individuals of differing backgrounds and levels of training. Failure to achieve tracheal intubation, resulting in the airway tube being placed in the esophagus and diverting air flow from the lungs, can cause patient complications (morbidity) or death (mortality) and is a continuing source of clinicians' anxiety.

The problem is acute because there are an estimated 18 million surgeries performed under general anesthesia each year in the United States alone. In addition, one million acute heart attack patients and three million trauma patients are admitted to hospitals each year. Most of these patients require mechanical ventilation and thus require tracheal placement of an airway tube.

In addition, there are other situations, typically in the field, where intubations are performed by paramedics or other individuals with less background and training than is typically found among hospital personnel. Misplacement of airway tubes (unrecognized esophageal intubation) by these individuals also contributes significantly to morbidity and mortality statistics.

A review of various anesthesia-related morbidity and mortality statistics indicates that unrecognized esophageal intubation is a problem, even among those members of the medical population specifically trained in the tracheal intubation technique. An analysis of anesthetic accidents reported to the Medical Defense Union of the United Kingdom from 1970-1978 revealed that nearly half of the cases resulting in death or cerebral damage were due to faulty clinical technique. The procedure most often identified as the source of mishap was tracheal intubation with inadvertent esophageal—rather than tracheal—tube placement.

Another reviewer of anesthesia-related medical liability claims in the United Kingdom from 1977 to 1982 listed esophageal intubation as a "main cause" of accidents leading to death or neurologic damage with the largest monetary claims resulting from such mishaps.

An investigation of anesthesia-related deaths in Australia revealed that 69% of these deaths were related to airway mismanagement with esophageal intubation once again identified as a major contributing factor.

In one institution in the United States, unrecognized esophageal intubation was identified as a significant problem in a study of cardiac arrests that had been attributed solely to anesthesia. There were twenty-seven cardiac arrests among 163,240 anesthetic cases over a fifteen year period. Of these twenty-seven cardiac arrests, four were attributed to esophageal intubation.

In the state of Kansas, five malpractice cases involving improper intubation were settled for one million dollars each in 1984-85. Four new cases alleging improper intubation were brought before Kansas courts in the first six months of 1986; at issue were two deaths and two brain-damage cases, all involving patients who were having elective surgeries.

In reviewing malpractice claims brought against anesthesiologists in Washington State from 1971-1982, researchers found that esophageal intubation figured prominently among complications resulting in cardiac arrest, brain damage, and death. Of 192 claims, seven were brought for unrecognized esophageal intubation.

The foregoing makes it clear that a reliable technique for confirming that tracheal intubation has been achieved would be of signal importance to the medical profession. Techniques providing signs which may, in some circumstances, indicate that a successful tracheal intubation has been accomplished include the following:

Direct Visualization

Direct visualization of the vocal cords and observation as the airway tube passes into the trachea is considered by many the "gold standard" of correct tube placement, and this remains one of the more reliable signs.

Unfortunately, direct visualization is impossible to achieve in certain patients, even in the most experienced hands, due to a multitude of factors. Clinicians and medics are thus often called upon to make "blind" intubations in which the position or condition of the patient is such that the progress of the tube cannot be followed visually. For example, it may be dangerous to immediately move an accident victim, or there may be insufficient lighting where a patient has collapsed at home. "Blind" intubations are performed in the hospitals as well, especially in patients who are overweight or have anatomical abnormalities. The problem is more common is inexperienced hands and may be associated with haste, poor lighting, or an individual patient's anatomical abnormality. Often, the clinician's view may be obstructed by the advancing tube, by acute angulation of the airway in the back of the patient's throat, or by a loss of depth perception with monocular vision.

Even if visualization of the vocal cords and tracheal tube placement has been achieved, the tube may be inadvertently withdrawn from the trachea before or during securing of the tube or when moving the patient to the lateral or prone position. Additionally, radiographic studies have shown that flexion or extension of the neck can change tube positions as much as five centimeters, resulting in inadvertent extubation which may well not be observed by the clinician.

Chest Movement

Another commonly relied upon method of confirming tracheal intubation is observation of symmetric bilateral movements of the chest wall during ventilation. Some patients, however, have physical conditions in which ventilation is more than usually dependent on diaphragmatic movement as opposed to chest wall movement. Patients with large breasts, obesity, a barrel chest from lung disease, and other conditions tend to develop rigid chest walls. Chest movement can be difficult to evaluate in these circumstances, making assessment of proper tube position by chest expansion unworkable.

More importantly, movement of the chest wall simulating ventilation of the lungs can be seen even with the ventilating tube positioned in the esophagus. Distension of the stomach with air can cause outward movement, mimicking the downward movement of the diaphragm and outward movement of the lower chest. Escape of gas from the stomach through the esophagus with release of bag compression would allow the diaphragm to fall and would move the lower chest inward, creating the false impression that there is exhalation from the lungs. Confirmation of this phenomenon exists in numerous reports and studies. At least one study demonstrated chest movements "identical to those seen when the lungs were inflated" where, in fact, stomach ventilation had been established through an airway tube intentionally inserted into the esophagus.

Breath Sounds

The presence of bilateral breath sounds from a stethoscope placed over each of the lungs would seem to be a strong reassurance of proper tube position based on experience and common sense. However, the literature documents numerous cases involving experienced clinicians where apparently normal breath sounds were present with esophageal ventilation. Air passing through the esophagus has been noted to resemble coarse or tubular breath sounds, and it has been suggested that the combination of esophageal wall oscillation with gas movement and acoustic filtering can produce wheezes similar to the sounds arising from lungs ventilated mechanically or by hand.

Presence of Exhaled Tidal Volume

This method of confirming tracheal intubation can be uncertain because it is possible to have measurable tidal volumes of air moving in the airway tube during spontaneous respiratory efforts with the esophagus intubated and the trachea obstructed. Researchers have documented tidal volumes of up to 180 milliliters and peak flows of greater than fifty liters per minute under these circumstances.

Reservoir Bag Compliance

Another practice commonly employed is noting the characteristic feel of the reservoir bag associated with normal lung compliance during inspiration and the presence of expiratory refilling of the bag during hand ventilation. However, compliance varies widely from one person to another and within the same individual at different times. Repeated filling and emptying of the stomach with esophageal ventilation, leading to inflation and deflation of the breathing bag, can also be mistaken for pulmonary ventilation.

Airway Tube Cuff Maneuvers

With the cuff deflated, the higher pitched sound of air escaping around a tracheal tube, compared to the more guttural of leakage around an esophageal tube, has been used as a distinguishing feature. However, with the cuff of an esophageal tube located near the level of the cricoid cartilage, the distinction in air sounds may not exist. Also, palpation of the airway tube cuff in the neck to verify position has been reported to fail, perhaps because the easily distensible esophagus simply balloons outward with an inflated cuff inside it.

Air Escape

A less commonly performed procedure involves pressing sharply on the chest while listening over the tub=opening to detect "a characteristic feel and sound of expelled air." This procedure is unreliable because of the inability to distinguish between air expelled from the tracheal tube and: (1) air passing through or around an esophageal tube, or (2) esophageal air present from mask ventilation prior to intubation, or (3) air expelled from the nose.

Tube Condensation

Condensation of water vapor in the tube, although less likely with esophageal intubation, can occur and hence is not a reliable sign. Conversely, the absence of condensation normally seen with a tube positioned in the trachea would be reason to look for further proof of correct tube position.

Pulse Oximetry

Although useful in many situations, pulse oximetry may be an untimely indicator of esophageal intubation for several reasons. Researchers have noted normal functioning of a ventilator when connected to an esophageal tube. With the vocal cords relaxed, patients were studied after deliberate intubation of both the esophagus and trachea. Ventilation into the esophagus also caused some ventilation of the lungs, as evidenced by carbon dioxide recordings obtained from the open tracheal tube. This ventilation could significantly slow the onset of oxygen desaturation of the blood after esophageal intubation and could delay recognition of esophageal tube placement until surgery is in progress. Also, the practice of preoxygenation of patients prior to intubation can slow the recognition of an improper tube position using pulse oximetry because the patients' blood is highly saturated with oxygen at the start of the surgical procedure.

End-Tidal Carbon Dioxide Measurement

End-tidal carbon dioxide measurement offers perhaps the most reliable and simplest determination of proper tube placement. It involves the measurement of carbon dioxide concentration during the respiratory cycle. The reliability of carbon dioxide monitoring is based on the assumption that carbon dioxide can be reliably detected in patients with an intact pulmonary circulation and an intubated trachea whereas no carbon dioxide is present in gases exiting from an esophageal tube. Carbon dioxide can be detected initially with esophageal intubation when carbon dioxide has been forced into the stomach during prior mask ventilation. However, the end-tidal carbon dioxide is low in such cases; the wave pattern is irregular; and the carbon dioxide levels rapidly diminish with repeated ventilation, making it easy to distinguish between carbon dioxide from the trachea and that from the esophagus.

The disadvantage of this test is that it takes a relatively expensive monitoring device. Also, this device is too cumbersome for routine use in all settings where it would be needed; and it must be connected to an electrical power source during the intubation procedure. This is disadvantageous because power may not be available where, or when, intubation is needed.

In short, the position of the airway tube employed to achieve tracheal intubation of a patient and thereby manage his or her airway must be checked on each insertion; and there are a large number of tests available to confirm tracheal placement of the tube. However, considerable evidence challenges the relative merits of these heretofore available tests. Also, there has been, up to now, no single device which can or would be used in all situations to detect misplacement of airway tubes in the esophagus. Furthermore, clinical studies have shown that, even with the detection of seemingly proper signs by experienced clinicians, an airway tube may have been placed in the esophagus. Also, a number of the just-discussed techniques for confirming tracheal intubation employ monitoring devices; and those devices each lack one or more of the following attributes, all of which are either required for the monitoring device to be successful or important in obtaining this goal:

Ease of use

The device must be easy to connect to the airway tube, require no more than minimal interpretation of the indication, and require no electrical power.

Sensitive

The device must display an obvious indication of carbon dioxide expired from the lung within thirty seconds.

Reliable

The indicator must not give false-positive readings but may show transitory readings from a limited volume of carbon dioxide or other materials from the stomach.

Inexpensive

The device should desirably sell for less than $1.00 U.S. in large quantities.

Disposable

To avoid cross-contamination, the device should be designed for single patient use.

Clean

The device should be designed to be cleaned during assembly in accordance with ANSI Code 279.2 for tracheal tube connectors and adapters.

Save

The device must not allow components to which it is attached to become disconnected or otherwise impede the normal ventilation of the patient.

Rugged

The device must withstand severe stresses without disconnecting from its mating tube.

Storable

The device must have a shelf life of twenty-four months prior to use without loss of effectiveness.

From the foregoing, it can be seen that undiagnosed esophageal intubation figures prominently in anesthesia-related morbidity or mortality and related malpractice suits. The commonly utilized methods of assessing tube position are all unsatisfactory under the circumstances encountered in tracheal tube placement. Expired carbon dioxide measurement is currently the most reliable means under all circumstances of determining proper tube position, but this method suffers from the requirement that an expensive monitoring device be attached to the airway tube before correct placement can be verified. Thus, the usefulness of this procedure in emergency conditions is limited; and it is relegated to formal hospital settings. There is no inexpensive product currently available which provides a simple test for carbon dioxide expired by the patient through the airway tube to verify tracheal tube placement.

SUMMARY OF THE INVENTION

There have now been invented, and disclosed herein, certain new and novel methods that employ devices which are usable in all known circumstances to provide a positive, reliable indication that tracheal intubation has been achieved.

The novel devices disclosed herein, and the methods in which they are employed, operate on the principles that: (1) after a few breaths, at most, carbon dioxide will appear in the intubated patient's exhalations at a threshold level (typically three percent) commensurate with tracheal intubation only if the airway tube has been placed in the patient's trachea and not his or her esophagus, and (2) this end-tidal carbon dioxide in a concentration which equals or exceeds the threshold value can be employed to effect an easily observed change in a characteristic of an appropriate indicator.

One embodiment of the invention which takes advantage of and can be employed to effect such a change in an indicator characteristic and which operates on the principles just described consists of a molded plastic housing, a reservoir of unreacted indicator solution, a reaction medium (or wick), and a sink for the reacted solution. To prepare the detector for use, the user pulls an activator tab or lanyard, breaking a reservoir seal and exposing the solution to the reaction medium. The solution thereupon immediately begins to wick (or migrate) across the reaction medium toward the sink. The clinician then connects the detector to the exposed end of an endotracheal tube just previously placed in the patient's airway. A ventilator is then connected to the other end of the detector to complete the patient's breathing circuit. As the ventilator forces air in and out of the endotracheal tube, any carbon dioxide in the patient's breath over or a three percent or other threshold concentration reversibly hydrates in the indicator solution and brings about a change in the color of the indicator solution migrating across the reaction medium toward the sink. This color change is monitored by the clinician.

If the endotracheal tube were misplaced in the esophagus, carbon dioxide trapped in the stomach or the esophagus might cause a color change in the indicator solution on the reaction medium. As the carbon dioxide in the breath decreases, however, and more solution migrates across the medium from the reservoir, the color would tend to change back to its initial hue. The continued presence of the unreacted color would warn the clinician that air from the lungs was not being carried by the tube and that the tube may be misplaced. If the tube is properly placed, the newly wicked solution reacts with the carbon dioxide coming from the lungs and quickly and definitely changes color. This detector gives a continuous indication of the presence of carbon dioxide for approximately fifteen minutes after the device's seal is broken.

Another important and representative embodiment of the invention employs a thin body of indicator solution trapped between a housing and a liquid-tight membrane of a material which is permeable to uncharged molecules but not to charged molecules or ions. One such material is Teflon (tetrafluoroethylene polymer). Carbon dioxide in expired gases flowing through the detector diffuses across the permeable membrane and then undergoes reversible hydration in the indicator solution, generating excess hydrogen (H+) ions and thus reducing the pH of the solution. This causes the indicator to change color, provided that the concentration of carbon dioxide in the expired gases has reached the threshold level and the pH of the solution has consequently been reduced to a level at which the indicator will change color. Thereafter, and between exhalations: the hydration of the carbon dioxide reverses, the carbon dioxide comes out of solution and diffuses back across the membrane, and the indicator tends to revert to its original color. Sustained periodic changes of color are an indication of successful tracheal intubation. If esophageal intubation has instead been achieved, the indicator may change color once or a very few times. Thereafter, however, it will tend to revert to and remain its initial color.

Because the membrane employed in detectors constructed as disclosed herein passes only uncharged molecules (in this case carbon dioxide), and not hydrogen ions or other charged particles, the membrane keeps charged particles not attributable to the reversible hydration of carbon dioxide from triggering an indicator color change and thereby perhaps providing a false indication of proper endotracheal tube placement.

The indicator solutions employed in the practice of the present invention may include an oxidation sensitive constituent such as a carbonic anhydrase catalyst. If incorporated in the solution, it can prove difficult, and expensive, to keep the oxidation sensitive material from deteriorating over a storage period of acceptable length. However, at least in the case of carbonic anhydrase, the perishable material is also available as a freeze dried powder and, in that form, can be stored indefinitely without deterioration.

In yet another and also very important embodiment of the invention, selected components of the indicator solution, such as the just-discussed carbonic anhydrase catalyst, are therefore supplied in a dry, more stable form and are mixed with the fluid phase of the solution only as the carbon dioxide detector is readied for use. This can be accomplished by placing the dry and liquid components of the indicator solution in separate, communicable, detector compartments; rupturing a seal between those compartments to establish communication therebetween when the detector is readied for use; and then shaking the detector to disperse the dry components of the solution (the solute) in the fluid carrier. As this dispersion proceeds, the color of the solution will develop, providing a clear indication to the user of the detector that it is ready to be used.

Alternatively, the material to be protected can be stored on a wick and a fluid phase containing the remaining constituents of the indicator solution put in a capsule. The capsule is loaded in a cavity having fluid communication with the wick. To ready the detector for use, the capsule is ruptured; and its contents are transferred to the wick, preferably under pressure. The fluid phase of the solution then migrates across the wick, incorporating into the indicator solution the relatively perishable material theretofore separately stored on the wick.

Embodiments of the invention of the character just described thus eliminate the above-discussed shelf life problem in a simple yet elegant fashion because the catalyst and any other perishable components are stored in a dry, stable form until the carbon dioxide detector is readied for use.

The foregoing and other embodiments of the invention are simple and inexpensive, and it is therefore practical to dispose of them after a single use.

Due at least in part to their simplicity, detectors employing the principles of the present invention are rugged, reliable, and easy to use; and they are sensitive to changes in the concentration of carbon dioxide in the gases being monitored. These detectors are simple to use because they employ easily made connections to an airway (or endotracheal) tube or adapter and to the hose of a mechanical ventilator, do not require any electrical connections, and require only minimal interpretation of the indications the device provides.

These novel devices can be easily monitored—even, for example, in a dimly lit room, using only a pen-sized flashlight. Response times are rapid; changes in the indicator evidencing tracheal placement of the endotracheal tube are forthcoming in 30 seconds or less (4–7 human breaths).

Response times on the order of those just described are desirable as, if they are achieved, monitoring devices of the character disclosed and claimed herein will function reliably to distinguish between tracheal and esophageal intubation even if the intubated patient is hyperventilating and the level of carbon dioxide in the patient's exhalations is thereby lowered.

Monitoring devices employing the principles of the invention are also safe because they are designed to provide secure connections between the device and the components to which it is attached—typically, as indicated above, an adapter at the exposed end of the airway tube and one end of the ventilator hose tube. There is consequently little chance that the airway tube will come loose and be lodged in the patient's trachea or interfere with the ventilation of the patient or the administration of anesthetics or other gases, etc. or that the ventilator hose will be detached and pose similar problems.

By virtue of the materials from which they are fabricated and the fact that the indicators and associated substances employed in the practice of the present invention can be provided in stable form and isolated from the ambient surroundings, monitoring devices employing the principles of the invention have a long shelf life.

The design of the novel monitoring devices disclosed herein is such that they are clean at the end of the manufacturing process, and their design also minimizes the possibility of foreign matter being introduced into the device from the ambient surroundings and subsequently entering a patient's lungs.

It is important, in employing the monitoring of carbon dioxide to determine proper airway placement, to distinguish between carbon dioxide expelled from the patient's lungs and carbon dioxide expelled from his or her stomach and esophagus as these anatomical structures may contain enough carbon dioxide to cause the monitoring device indicator to undergo a change in character and thus provide a potentially false indication of proper airway tube placement. As suggested above, this important distinction is made in accord with the principles of the present invention by employing a reversible indicator—i.e., one which will change in color (or other observable characteristic) when the threshold concentration of carbon dioxide is reached and revert toward its original color when the carbon dioxide concentration in the gases being monitored decreases to a lower level. The indicator characteristic will consequently change repeatedly (viz., with each exhalation) if the airway tube is placed in the patient's trachea. In contrast, there will be only a single cycle of change or a very few such cycles if the tube is improperly placed in the patient's esophagus as the expelling of the carbon dioxide from the patient's stomach and esophagus is a very short time phenomenon.

The change in indicator character indicative of a threshold level of carbon dioxide in the gases being monitored is brought about by the reversible hydration of carbon dioxide in an indicator solution to produce excess hydrogen ($H^+$) ions and a consequent reduction in the pH of the indicator solution. Also relied on is the dehydration that occurs when the concentration of carbon dioxide in the reaction situs decreases—during inhalation, for example—to effect an increase in the pH of the indicator solution and a consequent reversion in the color of that solution to its original color. In particular, it was pointed out above that a sustained series of color changes as just described can be employed to confirm that intubation of a ventilated patient has been achieved.

The reversible hydration of carbon dioxide proceeds slowly; and the hydration is preferably catalyzed—as with the above-mentioned carbonic anhydrase—so that the indicator will react fast enough to be acceptable to the medical profession; viz., provide an indication commensurate only with proper tube placement in 30 seconds or less.

Buffering can be employed to alter the threshold concentration of carbon dioxide required to trigger a change in the character of the indicator.

OBJECTS OF THE INVENTION

From the foregoing it will be apparent to the reader that one important and primary object of the present invention resides in the provision of novel, improved devices and methods for monitoring the concentration of carbon dioxide in a specified environment.

Another important and related, but more specific, object of the invention resides in the provision of methods and devices in accord with the preceding object which employ: (1) the reversible hydration, in an indicator solution, of carbon dioxide in the gases being monitored to produce excess $H^+$ ions and reduce the pH of the solution, and (2) the use of an indicator which changes character (typically color) when the concentration of such ions reduces the pH in a solution containing the indicator to a level commensurate with a threshold level of carbon dioxide to provide an indication that that level of carbon dioxide has been reached in the gases being monitored.

Another important and primary object of the present invention is the provision of novel, improved methods and devices for ensuring that an airway tube has been placed in the trachea of an intubated patient.

A related, also primary and important object of the invention resides in the provision of devices and methods as characterized in the preceding object in which the concentration of carbon dioxide in the gases flowing through the airway tube is monitored to insure that the airway tube has been properly placed.

A related and also important and primary object of the invention is the provision of methods and devices in accord with the preceding object in which the carbon dioxide expired by the patient is monitored in a manner that clearly distinguishes between: (1) the reaching of threshold levels of carbon dioxide due to proper placement of the airway tube in the patient's trachea, and (2) the reaching of that same level due to the presence in the monitored gases of carbon dioxide expelled from the patient's stomach and/or esophagus.

Other important objects and features and additional advantages of the invention will be apparent to the reader from the foregoing and the appended claims and as the ensuing detailed description and discussion proceeds in conjunction with the accompanying drawing.

DESCRIPTION OF THE INVENTION

Figure 1:
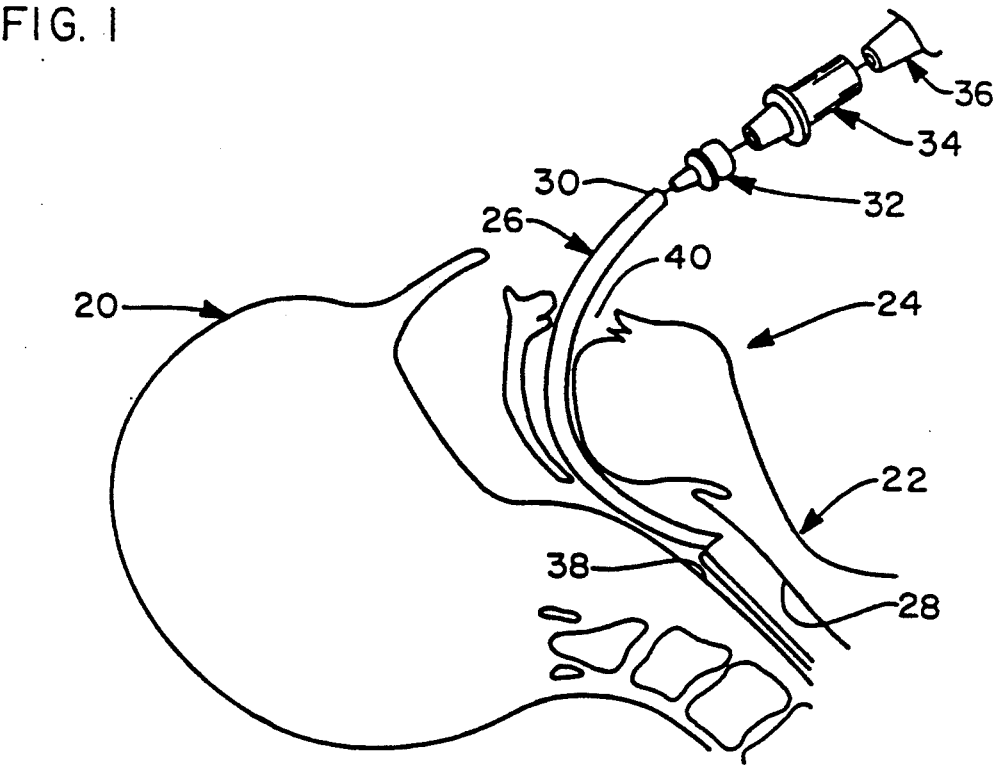
FIG. 1 is a pictorial view of a supine patient with an airway tube placed in his trachea and connected to a mechanical ventilator by way of a carbon dioxide detector as disclosed herein to confirm tracheal intubation in accord with the principles of the present invention.

As discussed above, the novel detectors disclosed herein and employed in the likewise disclosed methods of detecting carbon dioxide provide a visual indication, typically by effecting a color change in an appropriate indicator, if the carbon dioxide concentration in a sample of gases supplied to the detector is at, or above, a threshold level. pH sensitive indicators are employed. Among those suitable for the purposes of the present invention are:

Napthal Red
Phenol Red
Cresol Red
m-Cresol Purple
Bromothymol Blue
Bromophenol Blue
Brilliant Yellow
p-Nitrophenol
2,5-Dinitrophenol
Litmus Mixtures of the foregoing and/or other indicators may also be employed.

The color changes undergone by all of the foregoing indicators in the face of a decreasing pH are reversible; and the indicator will accordingly tend to revert to its initial color if the pH rises to a level above that triggering the color change. As discussed above, this is an important part of the invention as periodic, exhalation-related color changes can be employed to distinguish proper placement of an airway tube from placement of the tube in the patient's esophagus (both placements can result in sufficient carbon dioxide being circulated to the detector to produce a single or very small number of indicator color changes).

During exhalation, carbon dioxide in the intubated patient's expired breath is reversibly hydrated in the indicator solution, producing excess hydrogen ions. These ions lower the pH of the indicator solution, causing the indicator to change color as discussed above.

During inspiration, the gases flowing through the monitoring device are substantially devoid of carbon dioxide; and those gases are therefore not capable of causing the indicator to change color or causing it to retain the color it assumes when the pH in its environment is reduced. As a consequence, during inspiration, the indicator tends to revert to its original color. Therefore, by contacting aliquots of the indicator solution alternately with exhaled and then inspired breaths, the indicator solution will alternately change color and revert to its original color. A sustained series of these color change cycles indicates that the airway tube has been placed in the patient's trachea. In contrast, if esophageal intubation has instead been achieved, there may be one or even a very few color changes; but the solution will thereafter continuously remain the initial color it assumes in the absence of a color change triggering concentration of hydrogen ions. This clearly indicates that the airway tube has erroneously been placed in the patient's esophagus.

For example, in those embodiments of the invention employing a body of indicator solution behind a gas permeable membrane, dissolved carbon dioxide will come out of solution and diffuse out through the membrane during inspiration; and the indicator consequently tends to revert to its initial color. In this type of monitor, therefore, the color of the indicator will change with each inspiration and exhalation if the airway tube is properly placed in the patient's trachea. If the patient is instead the victim of improper esophageal intubation, there may be one to a few indicator color changes; but the indicator will thereafter tend to revert to and remain its original, unchanged color.

The color changes undergone by Cresol Red are typical. A three percent concentration of carbon dioxide (volume percent based on dry air) will cause this indicator in aqueous solution to change from purple to yellow. In vivo experiments showed that one to three breaths by pigs would result in sufficient build-up of carbon dioxide in the indicator solution to effect a useful color change of this indicator. Initial color changes occurred in 5-10 seconds and complete color changes in 20-40 seconds.

The reversible hydration resulting in the indicator color change and the subsequent reversion of the indicator to its original color when carbon dioxide is subsequently removed from the reaction site—both typically relied upon to verify tracheal intubation—may proceed more slowly than what is believed to be optimal. Consequently, a catalyst is preferably employed to speed up these reactions so that the response time of the detector will be within the limits specified above. Catalysts that one may employ include:

Carbonic Anhydrase
NaOCl
Na Selenite
$Na_2SO_3$

The presently preferred catalyst is the zinc metalloenzyme, carbonic anhydrase. This enzyme has at least three distinct isozymes, which can be obtained from a wide variety of human, other animal, and vegetable sources. Carbonic anhydrase obtained from bovine erythrocytes has proven suitable. However, the catalytic mechanism of the different isozymes of carbonic anhydrase appears to be the same (see Silverman et al., The Catalytic Mechansim of Carbonic Anhydrase: Implications of a Rate-Limiting Protolysis of Water, 21 Accounts of Chemical Research, The American Chemical Society, Jan., 1988, pp. 30 et seq.). Consequently, it is not intended to exclude from the patent coverage sought herein the use of carbonic anhydrase isozymes obtained from other sources—parsley or spinach, for example—or synthetic isozymes of the carbonic anhydrase.

Particularly if carbonic anhydrase is employed to catalyze the reversible hydration of carbon dioxide, a stabilizer for the catalyst may be required. Glycerol and propylene glycol are examples of appropriate stabilizers.

Also, a preservative will typically be required to protect the carbonic anhydrase enzyme against attack by fungi and bacteria. Parabens (methyl, propyl, butyl, and ethyl esters of para-hydroxybenzoic acid) are suitable for this purpose.

The selected catalyst can be mixed with the indicator solution.

Alternatively, as discussed above, the carbonic anhydrase can be provided in the form of a freeze-dried powder, a form in which that enzyme is very stable, and mixed with the indicator solution in which the carbon dioxide is reversibly hydrated only when the carbon dioxide detector is readied for use.

Additionally, buffers may be added to the indicator solution, as appropriate. These compositions alter the concentration of hydrogen ions required to lower the pH of the solution to the level at which the indicator will change color. By thus adjusting this parameter, one can define the threshold concentration of carbon dioxide required to effect a change in the color of the indicator. This allows one to structure the monitoring device so that: the indicator will change color with each exhalation even if the intubated patient is hyperventilating or the concentration of carbon dioxide in his expired breaths is otherwise relatively low and to otherwise adjust the response of the indicator to specified concentrations of carbon dioxide and define its sensitivity to specified concentrations of carbon dioxide.

Buffers that have been employed for the foregoing purposes include aqueous solutions of: (1) sodium barbital and HCl, (2) $NaHCO_3$, and (3) NaOH.

Similar adjustments in sensitivity, response time, etc. can also be obtained by employing a different indicator as the pH and pH range to which pH sensitive indicators respond are typically different.

Referring now to the drawing, FIG. 1 depicts the head 20 and upper body 22 of a supine patient 24 and an airway or endotracheal tube 26 placed in the patient's trachea 28. The exposed or outer end 30 of the endotracheal tube 26 is connected by an adapter 32 to a detector 34: (1) embodying the principles of the present invention, and (2) provided to detect threshold levels of carbon dioxide in the breaths exhaled by patient 24. As is shown in FIG. 1, the carbon dioxide detecting device 34 is connected in line between endotracheal tube 26 and the hose 36 of a mechanical ventilator (not shown).

As is readily apparent from FIG. 1, a human's esophagus (identified by reference character 38) lies immediately adjacent the patient's trachea 28. As a consequence, an endotracheal tube such as that identified by reference character 26 and introduced through the patient's mouth 40 can easily be placed in esophagus 38 rather than trachea 28, even if care is exercised in placing the tube and the conditions under which the tube is placed are optimal. And it was pointed out above that it is often difficult to ascertain by heretofore available techniques whether the endotracheal tube has been properly placed and that undetected esophageal intubation of patients has occurred with astonishing regularity with consequent morbidity and more than occasional mortality.

It was also pointed out above that carbon dioxide detector 34 substantially eliminates this hazard, even when an endotracheal tube is placed under adverse conditions or by a less than highly trained or skilled individual, because it provides an unmistakable differentiation between tracheal and esophageal intubation. In particular, when carbon dioxide monitoring devices of the character shown in FIG. 1 and identified by reference character 34 are utilized, an indicator of the character discussed above changes color each time the patient 24 exhales; and the indicator tends to revert to its original (or initial) color between exhalations. If tracheal intubation has been achieved, these changes in color will continue over an extended period of time. In contrast, if the endotracheal tube 26 has instead been placed in the patient's esophagus, a reversible color change may occur concomitantly with the patient's first breath, and may continue for a few breaths, because of the presence of carbon dioxide in gases expelled from the patient's esophagus and/or stomach. Thereafter, however, the indicator will tend to revert to and remain its original color, clearly indicating that esophageal as opposed to tracheal intubation has been achieved.

Figure 2:
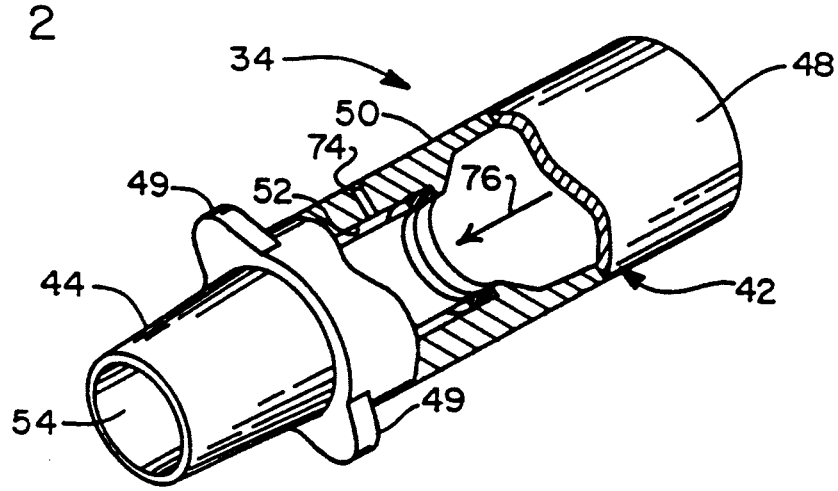
FIG. 2 is a perspective view of the carbon dioxide detector with part of the detector casing broken away to show its internal construction.
Figure 3:
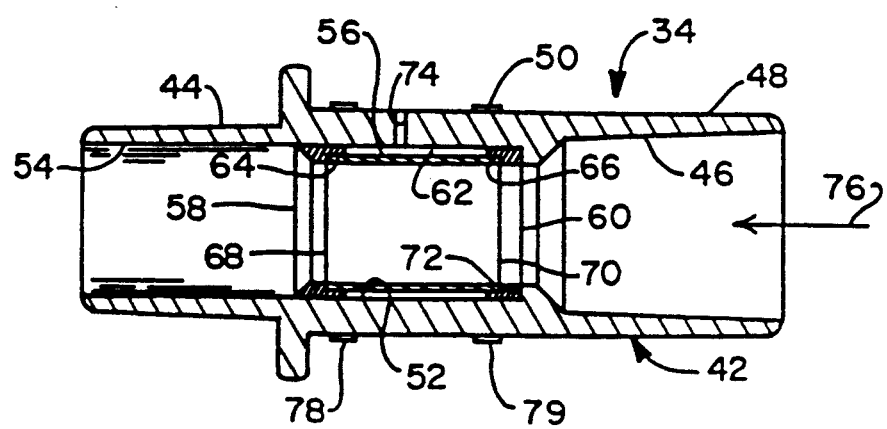
FIG. 3 is a longitudinal section through the detector.

Referring now to FIGS. 2 and 3, carbon dioxide detector 34 includes an elongated, hollow, cylindrical, circularly sectioned housing 42 molded or otherwise fabricated from a clear synthetic polymer such as a polyethylene. A typical detector of this character is one and one-half inches long and 15 millimeters in diameter.

An externally tapered shoulder 44 at one end of housing 42 and an internally tapered aperture or recess 46 in the opposite end 40 of that housing, both conforming to ANSI Standard 279.2, respectively accept ventilator hose 36 and endotracheal tube adapter 32 and provide secure connections between those components and the carbon dioxide detector. This ensures, with a high degree of reliability, that the connections between endotracheal tube 26 and the mechanical ventilator will not be interrupted, a consequence that is to be avoided because of the danger this would pose to the intubated patient.

Tabs 49 extend radially and in opposite directions from detector housing 42. Rubber bands (not shown) can be trained over these tabs to ensure that the connections of the monitoring device 34 to the endotracheal tube 26 and ventilation hose 36 are maintained.

Midway between the end sections 44 and 48 of housing 42 is a central section 50. An annular groove 52 is formed in this central section 50 of housing 42, and this groove opens onto the bore 54 through housing 42.

As is best shown in FIG. 3, a cylindrical membrane 56 and circular seals 58 and 60 cooperate with the groove 52 in the central section 50 of housing 42 to define a sealed, annular plenum or cavity 62. Seals 58 and 60 have annular recesses 64 and 66 in which the opposite ends 68 and 70 of membrane 56 are seated. The resulting assemblage of that membrane with seals 58 and 60 is installed in housing 42 in spaced relation to the inner end of groove 52 and with seal 60 butting against an internal, annular flange 72 in housing 42.

The sealed chamber thus provided by the cooperation among housing 42, membrane 56, and circular seals 58 and 60 is filled with an indicator solution of the character described above. This may be done by injecting that solution with a hypodermic needle through a port 74 in detector housing 42. The injection port is thereafter sealed in any convenient fashion (sealing may be unnecessary, especially if housing 42 is made from a self-sealing material).

As discussed above, membrane 56 is preferably fabricated from a liquid-tight material which is permeable to uncharged compounds such as carbon dioxide but impermeable to charged particles such as hydrogen ions. Twelve micrometer thick Teflon is satisfactory.

With carbon dioxide detector 34 coupled to and between mechanical ventilator hose 36 and endotracheal tube adapter 32 as shown in FIG. 1, gases exhaled by patient 24 will flow from endotracheal tube 26 through detector 34 in the direction indicated by arrow 76 in FIGS. 2 and 3. Carbon dioxide in the gases exhaled by patient 24 diffuses across membrane 56 into the indicator solution filling cavity 62, this cavity therefore also serving as a reaction chamber. As discussed above, the carbon dioxide reversibly hydrates in the indicator solution to form excess hydrogen ions. If the concentration of carbon dioxide in the exhalations flowing through detector 34 is at or above a threshold level, the reversible hydration of the carbon dioxide and the resulting build-up of hydrogen ions in the indicator solution will lower the pH of that solution to a level at which the indicator in the solution will change color. Thereafter, and until the next exhalation of patient 24, the hydration reactions will reverse when carbon dioxide comes out of the indicator solution, decreasing as the concentration of that compound in the detector decreases. This carbon dioxide diffuses across membrane 56 back into the bore 54 through detector 34. As this occurs, the concentration of hydrogen ions in the indicator solution will decrease, the pH of that solution will rise, and the indicator will consequently tend to revert to its original color.

Thus, the indicator in the solution trapped in cavity 62 will change color with a frequency approaching that with which patient 24 breaths. If these reversals in color occur for more than a very few breathing cycles, it can safely and reliably be assumed that tracheal intubation has been achieved. This is because, if esophageal intubation has instead been achieved, indicator color changes will not occur after whatever carbon dioxide might be present has been expelled from the patient's stomach and esophagus; and this occurs, at the latest, after only a very few exhalations. Thereafter, the indicator will tend to revert to its initial color and will remain the color to which it reverts, clearly indicating to the observer that esophageal rather than tracheal intubation has been achieved.

Because detector housing 42 is fabricated from a clear material, the just-described visual indications will be clearly evident to the individual monitoring the placement of airway tube 26.

Bands of color 78 and 79, shown in exaggerated form in FIG. 3, circle detector housing 42 at locations corresponding to the ends of the cavity 62 in which the indicator solution is trapped. One of these bands matches the initial color of the indicator; i.e., the color the indicator has when the carbon dioxide in the gases being monitored is below the threshold limit required to trigger a color change. The other band is matched to the color the indicator has when the threshold concentration is reached and the color change effected. Indicia associated with the bands (no shown) identify the association of those bands with the initial and changed colors, respectively. Thus, by merely looking at the indicia associated with the band matched by the indicator, the individual monitoring the detector can ascertain whether carbon dioxide is present in a threshold amount.

In a typical application of the invention employing cresol red as an indicator, one of the bands 78 and 79 will be purple to match the initial color of the indicator; and the other will be yellow, matching the color the indicator has when a threshold concentration of carbon dioxide is present or reached.

Figure 4:
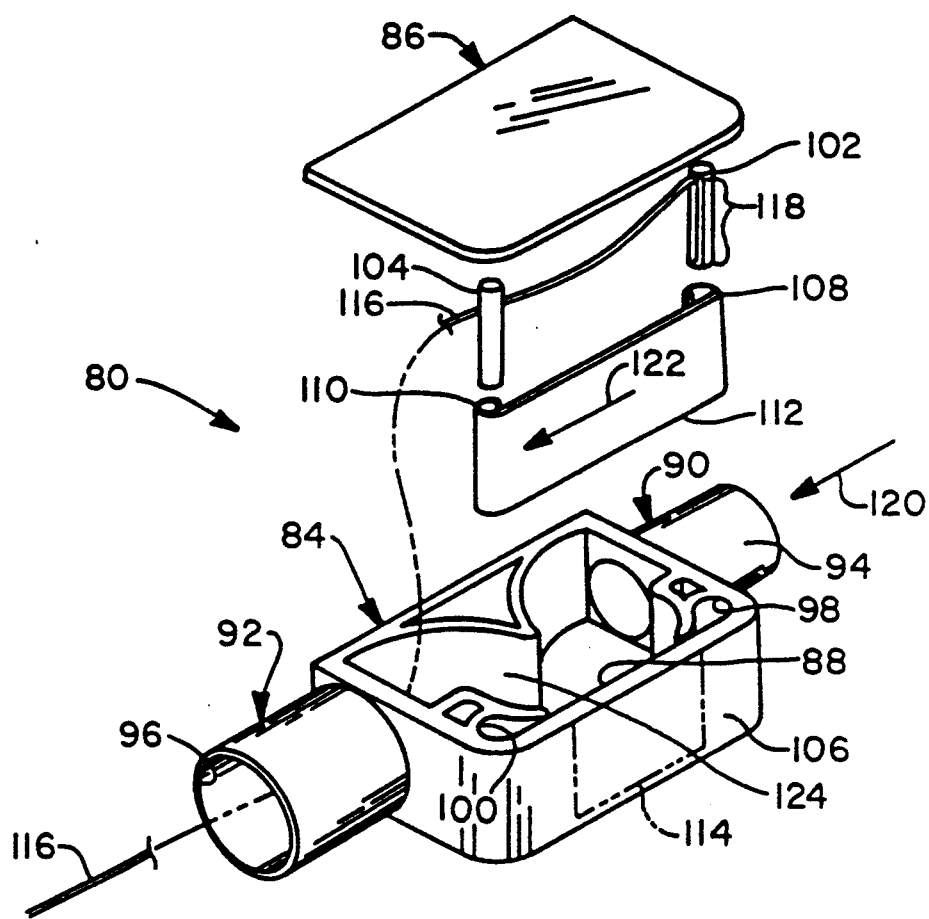
FIG. 4 is an exploded view of a second form of carbon dioxide detector which embodies, and can be employed in methods embodying, the principles of the present invention.
Figure 5:
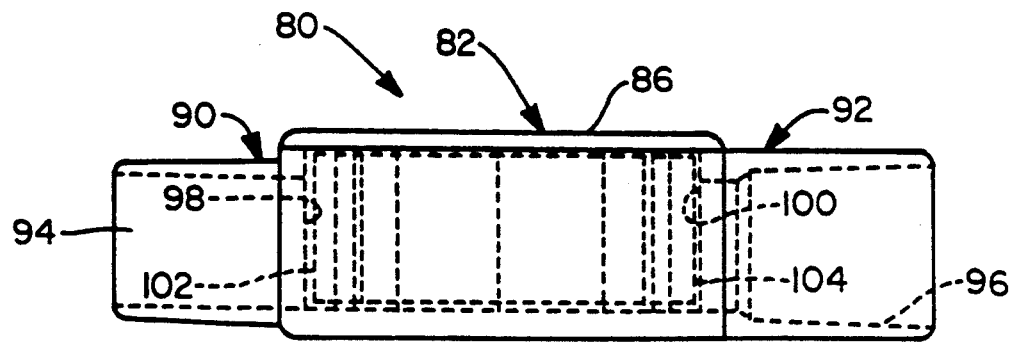
FIG. 5 is a bottom view of the carbon dioxide detector of FIG. 4.
Figure 6:
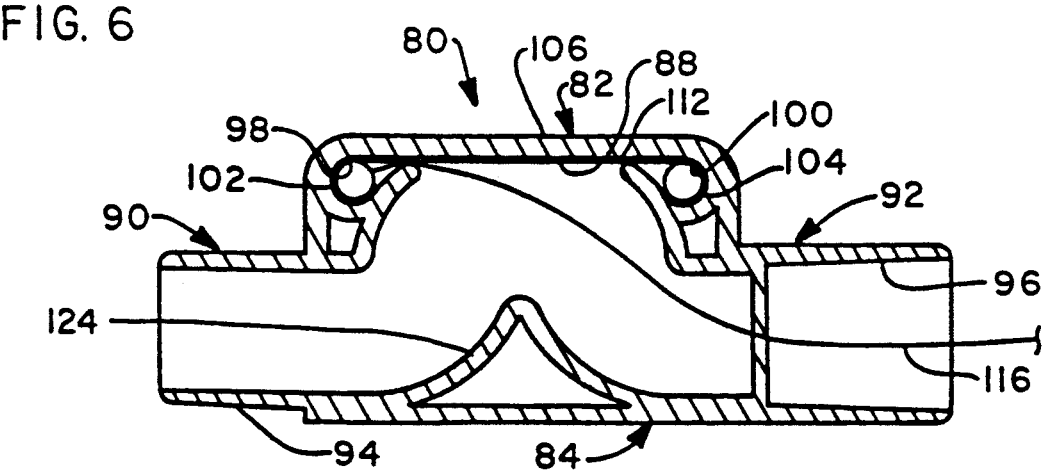
FIG. 6 is a longitudinal section through the detector of FIG. 4, taken substantially along line 6—6 of FIG. 5.

Referring still to the drawing, FIGS. 4–6 depict a second carbon dioxide detector 80 which also operates in accord with the principles of the present invention but in a somewhat different manner than the just-described detector 34 does.

Referring then to the Figures just identified, carbon dioxide detector 80 includes a housing or casing 82 having a main, boxlike member 84. A lid 86 can be sealed to casing member 84 after the internal components of the detector are installed to isolate the interior 88 of housing 82 from the ambient surroundings. This keeps the casing interior from being contaminated by foreign substances in the surrounding environment.

Inteqral bosses 90 and 92 at the opposite ends of main casing member 84 have external and internal tapers 94 and 96 which, like their counterparts 44 and 46 in adapter 34, provide reliable and secure connections between: (1) the carbon dioxide detector 80, and (2) the airway adapter 32 and mechanical ventilator hose 36 to which that detector is attached.

Supported in parallel, spaced apart recesses 98 and 100 in main casing member 84 are: (1) a reservoir capsule 102 filled with an indicator solution of the character described above, and (2) a member 104 can ascertain whether carbon dioxide is resent in a threshold amount.

In a typical application of the invention employing cresol red as an indicator, one of the bands 78 and 79 will be purple to match the initial color of the indicator; and the other will be yellow, matching the color the indicator has when a threshold concentration of carbon dioxide is present or reached.

Referring still to the drawing, FIGS. 4–6 depict a second carbon dioxide detector 80 which also operates in accord with the principles of the present invention but in a somewhat different manner than the just-described detector 34 does.

Referring then to the Figures just identified, carbon dioxide detector 80 includes a housing or casing 82 having a main, boxlike member 84. A lid 86 can be sealed to casing member 84 after the internal components of the detector are installed to isolate the interior 88 of housing 82 from the ambient surroundings. This keeps the casing interior from being contaminated by foreign substances in the surrounding environment.

Integral bosses 90 and 92 at the opposite ends of main casing member 84 have external and internal tapers 94 and 96 which, like their counterparts 44 and 46 in adapter 34, provide reliable and secure connections between: (1) the carbon dioxide detector 80, and (2) the airway adapter 32 and mechanical ventilator hose 36 to which that detector is attached.

Supported in parallel, spaced apart recesses 98 and 100 in main casing member 84 are: (1) a reservoir capsule 102 filled with an indicator solution of the character described above, and (2) a member 104 which functions as a sink for the indicator solution. Encapsulation or other packaging is employed to prevent evaporation and to keep the indicator solution from being contaminated.

Extending between these two components of detector 80 and along the side wall 106 of main casing member 84 with its opposite ends 108 and 110 respectively trained around reservoir capsule 102 and sink 104 is an elongated wick or reaction member 112. This wick is visible through a window 114 in casing member side wall 106. Window 114 may be provided by molding main casing member 84 from a clear plastic or by installing a window of such material in a casing member otherwise formed from a different material. Appropriate clear polymers are identified above and hereinafter.

Wick 112 will typically be fabricated from a conventional, commercially available, non woven, Nylon paper. Other materials with wicking capabilities may instead be employed; but it is, however, important that the wicking medium not be acidic. Otherwise, it might affect a change in the indicator solution not attributable to the presence of a threshold level of carbon dioxide, consequently keeping the carbon dioxide detector from working properly.

Member 104 can be made from an absorbent material such as a gauze sponge.

To employ detector 80, a lanyard 116 (see FIGS. 4 and 6) is pulled before the connection between detector 80 and endotracheal tube adapter 32 is effected. This ruptures reservoir 102 over a span indicated by reference character 118 in FIG. 4, allowing the indicator solution to flow onto and saturate that end 108 of wick 112 at reservoir 102.

An inteqral flow director 124 in housing 82 directs the gases into intimate contact with the indicator solution on wick 112 to promote the reversible hydration of carbon dioxide discussed above and, consequently, the ability of device 80 to detect carbon dioxide present in those gases.

Figure 7:
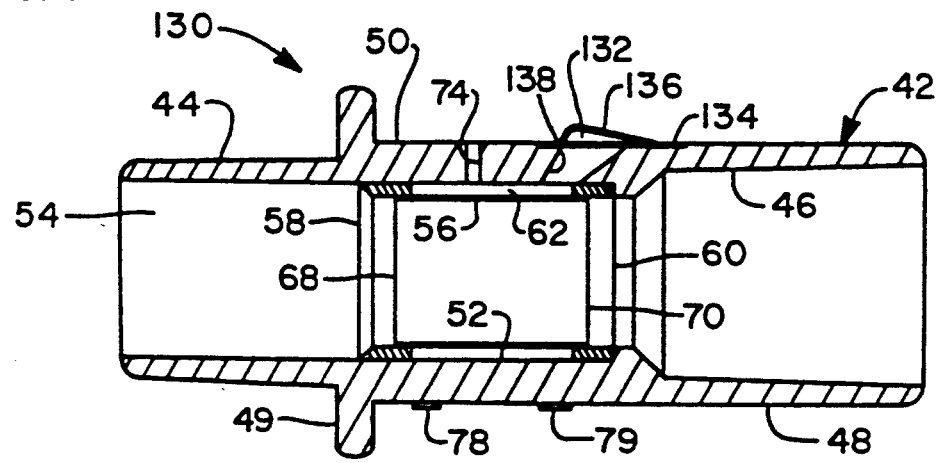
FIG. 7 is a longitudinal section through a third type of carbon dioxide detector which can also be employed in methods embodying the principles of the invention and is designed to have a long shelf life.
Figure 8:
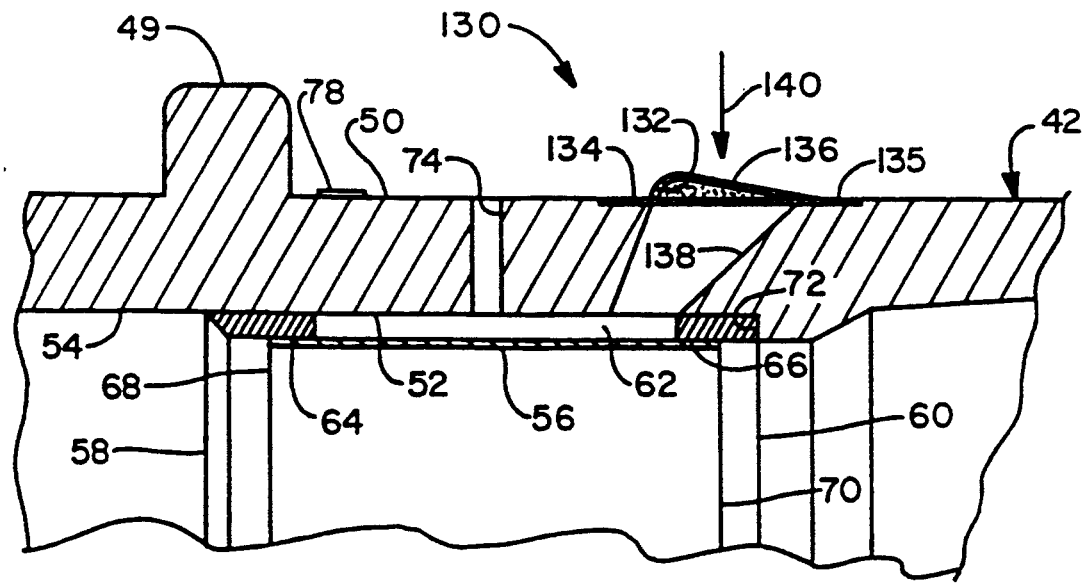
FIG. 8 is a fragment of FIG. 7 to a larger scale.

Referring still to the drawing, FIGS. 7 and 8 depict yet another carbon dioxide detector 130 embodying the principles of the present invention. This detector resembles the carbon dioxide detector 34 illustrated in FIGS. 2–4 and discussed above. To the extent that this is true, like components of detectors 34 and 130 have been identified by the same reference characters.

The carbon dioxide detector 130 illustrated in FIGS. 7 and 8 is furthermore like detector 34 in that an indication commensurate with a threshold level of carbon dioxide having been reached in a sample being monitored is produced by: (1) that carbon dioxide diffusing across a permeable membrane and undergoing reversible hydration in an indicator solution behind the membrane, and (2) a consequent generation of an excess of hydrogen ions in the indicator solution to trigger a change in the color of the indicator.

Indicator 130, however, does differ in a major respect from indicator 34 in that the solute (dry components, typically a pH sensitive indicator and a carbonic anhydrase catalyst) and solvent (typically water plus a buffer) of the indicator solution are not mixed until carbon dioxide detector 130 is readied for use. As discussed above, this is important with respect to the storage life prior to use of the detector because the indicator solution will typically contain one or more constituents which are much more stable in dry form then in aqueous solution.

In indicator 130, the typically but not necessarily aqueous, fluid phase of the indicator solution is injected into the sealed cavity 62 behind permeable membrane 56 through injection port 74. The remaining constituents of the indicator solution are furnished in a dry form and placed in a compartment 132. This compartment lies between a seal 134 located in a depression 135 in the central section 50 of casing 42 and a flexible push tab 136 fixed to that seal. A communicating channel 138 is provided through detector housing 42 between sealed compartment 132 and the sealed cavity 62 behind membrane 56.

To ready carbon dioxide detector 130 for use, one presses down on tab 136 (i.e., in the direction indicated by arrow 140 in FIG. 8). This ruptures the seal 134 at the outer end of channel 138, providing fluid communication between the sealed cavity 62 housing the fluid phase of the indicator solution and the cavity 132 housing those components of the indicator solution stored in dry form. The clinician or other user of carbon dioxide detector 130 then shakes that device to mix the components of the indicator solution and thereby disperse the dry components in the liquid carrier. This results in color being developed in the indicator solution, clearly indicating to the user of the device that the liquid and solid components of the solution have been intimately mixed.

Thereafter, carbon dioxide detector 130 functions in the same manner as the detector 34 discussed above.

In a typical carbon dioxide detector of the character disclosed herein, the constituents of the indicator solution will be the following:

Dry Phase: Indicator (Cresol Purple) 100 mg
Fluid Phase: Distilled Water 100 ml, 0.01 M NaOH (buffer) 50 ml.

It is not required, in conjunction with the preceding example, that the carrier of the indicator solution be an aqueous one. For example, the reversible hydration of carbon dioxide in ethanol is a well-documented phenomenom. The use of this compound and other fluids in which the reversible hydration of carbon dioxide can be carried out in the indicator solutions of the present invention is therefore intended to be covered in the appended claims unless expressly excluded therefrom.

Also, as was discussed above on more than one occasion, a catalyst—preferably a "dry" carbonic anhydrase isozyme or a mixture of such isozymes—can be added to the indicator solution to increase the speed with which the detector employing the indicator solution reacts to a change in carbon dioxide concentration. Storage of this catalyst and/or other perishable indicator solution constituents is optionally employed to increase the shelf life of the detector.

As indicated above and as will be apparent to those versed in the arts to which this specification is addressed, the foregoing, exemplary application of the invention (confirming tracheal intubation) is only one of many in which the principles of that invention can be employed to advantage. Other representative applications involve the monitoring of carbon dioxide levels in industrial processes and in enclosed working and/or living areas where accumulation of carbon dioxide can pose a hazard—on board submarines, for example.

Furthermore, the invention may be embodied in other specific forms without departing from the spirit or essential characteristics thereof. The embodiments of that invention discussed above are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. A method of confirming that an airway tube has been placed and is being maintained in the trachea of a patient, said method comprising the steps of:

preparing a detector means including an indicator which is sensitive to $CO_2$ at predetermined threshold concentrations occurring in exhalations of the patient and is so selected: (a) as to undergo in cycles matching successive breaths of the patient a sustained pattern of periodic changes of color representing, in an alternating manner: (i) the presence of a threshold concentration of $CO_2$ within the airway tube, and (ii) the absence of the threshold concentration of $CO_2$ within the airway tube but to (b) be incapable of undergoing such periodic changes of color in the absence of exhalations producing such alternating pattern of $CO_2$ concentrations in the airway tube;

so associating the detector means with the airway tube and thereby making said indicator responsive to gases in the airway tube that, if said tube is correctly placed in the trachea of the patient, said indicator will undergo said sustained pattern of periodic changes in contrast to the absence of a recurring pattern found when the detector means associated airway tube is mistakenly installed in the esophagus of the patient;

observing whether the detector means indicator undergoes the sustained pattern of periodic changes of color indicative of the placement and maintenance of the airway tube in the trachea of the patient or whether the sustained pattern of periodic changes is absent as is indicative of the airway tube having been dislodged or incorrectly placed in the patient's esophagus;

employing an observation of a sustained pattern of periodic changes of color as evidence that the airway tube has been placed and is being maintained in the trachea of the patient; and employing an observation that a sustained pattern of periodic changes of color is not present as evidence that the airway tube was not or is no longer correctly placed in the trachea of the patient.

* * * * *